US009239281B2

(12) United States Patent
Manri et al.

(10) Patent No.: US 9,239,281 B2
(45) Date of Patent: Jan. 19, 2016

(54) METHOD AND DEVICE FOR DIVIDING AREA OF IMAGE OF PARTICLE IN URINE

(75) Inventors: Chihiro Manri, Kawagoe (JP); Hideyuki Ban, Kodaira (JP); Satoshi Mitsuyama, Tokyo (JP); Norio Owada, Naka (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 648 days.

(21) Appl. No.: 12/920,424

(22) PCT Filed: Mar. 26, 2009

(86) PCT No.: PCT/JP2009/056135
§ 371 (c)(1),
(2), (4) Date: Aug. 31, 2010

(87) PCT Pub. No.: WO2009/125678
PCT Pub. Date: Oct. 15, 2009

(65) Prior Publication Data
US 2011/0002516 A1 Jan. 6, 2011

(30) Foreign Application Priority Data
Apr. 7, 2008 (JP) .................................. 2008-098866

(51) Int. Cl.
*G01N 15/14* (2006.01)
(52) U.S. Cl.
CPC .......... *G01N 15/147* (2013.01); *G01N 15/1475* (2013.01); *G01N 2015/1472* (2013.01)
(58) Field of Classification Search
CPC ............ G01N 15/147; G01N 15/1475; G01N 2015/1472
USPC ....................................................... 382/128
See application file for complete search history.

(56) References Cited

U.S. PATENT DOCUMENTS

| 5,068,906 | A  | * | 11/1991 | Kosaka .................. G06T 1/0007 382/133 |
| 5,121,436 | A  | * | 6/1992  | Kasdan ..................... G06T 7/00 382/128 |
| 5,768,412 | A  | * | 6/1998  | Mitsuyama et al. .......... 382/173 |
| 6,317,511 | B1 | * | 11/2001 | Horiuchi ............ G01N 15/1459 356/39 |

FOREIGN PATENT DOCUMENTS

| EP | 0556971 A2   | 2/1993  |
| JP | 63094156 A   | 4/1988  |
| JP | 1270177 A    | 10/1988 |
| JP | 1119765 A    | 5/1989  |
| JP | 3131756 A    | 6/1991  |
| JP | 5296915 A    | 11/1993 |
| JP | 8145871 A    | 6/1996  |
| JP | 10302067 A   | 11/1998 |
| JP | 2000-206027  | 7/2000  |

* cited by examiner

*Primary Examiner* — Sheetal R Paulson
(74) *Attorney, Agent, or Firm* — Baker Botts L.L.P.

(57) ABSTRACT

An objective is to provide a method and an apparatus for accurately extracting a region of an object particle from a urine particle image obtained by taking an image of urine particles in a urine specimen having varying properties. First, a first object region is extracted using one or more of an R image, a G image, and a B image of a urine particle image taken by an image input optical system configured to input particle images. Then, a density distribution and a size of the first object region of one or more of the R image, the G image, and the B image are calculated. Based on these feature parameters, the first object region is classified into a predetermined number of groups. A second object region is extracted from a local region including the first object region, by using one or more of the R image, the G image, and the B image, depending on each of the groups. This configuration allows stable region segmentation for each particle image even for a urine specimen in which urine particles having different sizes and tones coexist.

9 Claims, 10 Drawing Sheets

METHOD AND DEVICE FOR DIVIDING AREA OF IMAGE OF PARTICLE IN URINE

TECHNICAL FIELD

The present invention relates to a method for image region segmentation that uses density information, and particularly to a method and an apparatus for region segmentation favorable for segmentation of a urine particle image.

BACKGROUND ART

In a conventional method for morphological examination of particles in urine, an examination is performed by centrifugal separation of urine particles from collected urine, and then by direct observation of the urine particles by a laboratory technician through a microscope. Such microscopic examination has such problems that (1) the result depends on the proficiency of the technician and (2) examination takes time. Accordingly, a more efficient way is demanded.

In recent years, automation of an examination of urine sediments (urine particles) has been in progress. For example, "Particle Analysis Apparatus and Particle Analysis Method (Patent documents 1 and 2)" describes a method in which a urine specimen is passed through a specially-shaped flow channel (flow cell) to pass particles in the specimen through a wide imaging region, where an enlarged image of the urine particles is taken as a static image with a flash lamp lighted.

To automatically classify a urine particle whose image is taken as a static image, the image is first divided into a region with a urine particle and a background region, and the urine particle is classified based on image feature parameters obtained for the region with the urine particle.

"Region Segmentation Method for Particle Images (Patent document 3)," for example, describes a conventional technique for dividing an image into a region with a urine particle and a background region. In this conventional technique, a method is shown in which an object region is separated from a background region based on a threshold and the magnitude of change in density value, which are obtained from a density histogram.

In addition, "Patterning Recognition Apparatus (Patent document 4)" and "Automatic Blood Cell Classification Apparatus (Patent document 5)," for example, describe conventional techniques for classifying an object based on image feature parameters. In these conventional techniques, use of a layered network as a recognition logic is described.

[Patent document 1] JP 5-296915 A
[Patent document 2] JP 63-94156 A
[Patent document 3] JP 8-145871A
[Patent document 4] JP 10-302067 A
[Patent document 5] JP 3-131756 A

DISCLOSURE OF THE INVENTION

Problems to be Solved by the Invention

In a urine sediment examination apparatus, object particles for which region segmentation is performed vary from one another in their properties as shown below.

(1) In urine sediment examination, a urine specimen is often stained to facilitate determination on particles. Particles thus stained include sufficiently-stained particles (stained particles) and hard-to-stain particles (insufficiently-stained particles (light-stained particles) and hardly-stained particles (nonstained particles)).

(2) Even particles of the same type include sufficiently-stained particles and hard-to-stain particles.

(3) Particles having different tones coexist in a single image.

As described, object particles examined by a urine sediment apparatus vary in their properties. This brings a problem that accurate regions might not necessarily be extracted if a single region segmentation method is used for all the objects.

For example, the above-mentioned conventional region segmentation method (Patent document 3) discloses a method in which a background density distribution is estimated with the mode of a density histogram used as an average density of the background, and both a part darker than and a part lighter than the background density distribution are extracted as object regions. As to hard-to-stain particles, some pixels of an object region have density values lighter than those in the background due to light refraction and reflection within the object region. Accordingly, this method claims to be able to accurately extract the shape of a hard-to-stain cell by extracting the part lighter than the background, as well. However, there are cases where light reflection and refraction near a contour of an object cause a background region adjacent to the object to have a part much lighter than the average density of the background. Consequently, the background near the contour might be extracted as an object, which is one of factors of degrading the region segmentation accuracy.

Moreover, in the case of using the above-mentioned conventional region segmentation method (Patent document 3), an object region and a background region partially overlap in a density histogram of hard-to-stain particles. For this reason, in order to extract a region of such a particle, region segmentation needs to be performed with a smallest possible density range for the background region set in the estimation of a background density distribution. However, when a region with a sufficiently-stained particle is extracted using the same threshold as that used for hard-to-stain particles, a region which is really the background might be extracted as an object, which is another one of the factors of degrading the region segmentation accuracy.

An objective of the present invention is to provide a method and an apparatus for region segmentation by which stable region segmentation is performed for each particle in a urine specimen in which urine particles having different sizes and tones coexist.

Means for Solving the Problems

To solve the above described problems, a method for region segmentation of urine particle images is characterized by comprising the steps of: extracting a first object region by using one or more of an image with red components (hereinafter referred to as an R image), an image with green components (hereinafter referred to as a G image), and an image of blue components (hereinafter referred to as a B image) of a urine particle image taken by an image input optical system configured to input particle images; calculating a density distribution of one or more of the R image, the G image, and the B image in the first object region, and a size of the first object region, and classifying the first object region into a predetermined number of groups based on the density distribution and the size; and extracting a second object region from a local region including the first object region in the image, by using one or more of the R image, the G image, and the B image, depending on each of the groups. With the configuration, the first object region larger than a particle image is extracted. Then, the first object region is classified into the predetermined number of groups based on the tone and the size thereof. Based on the classification result, the second object region is extracted according to the features of the particle image. Thus, stable region segmentation can be performed for each particle image even for a urine specimen in which urine particles having different sizes and tones coexist.

Furthermore, a method for region segmentation of urine particle images is characterized by comprising: a first step of creating a density histogram of each of an R density, a G density, and a B density by using an R image, a G image, and a B image of a urine particle image taken by an image input optical system configured to input particle images, and obtaining one or more parameters indicating a shape of the density histogram; a second step of extracting a first object region by using the one or more parameters and one or more of the R image, the G image, and the B image; a third step of calculating a density distribution of one or more of the R image, the G image, and the B image in the first object region and a size of the first object region, and classifying the first object region into a predetermined number of groups based on the density distribution and the size; and a fourth step of extracting a second object region from a local region including the first object region in the image, by using the one or more parameters and one or more of the R image, the G image, and the B image, depending on each of the groups. Performing threshold processing using density histograms offers such an effect that stable threshold processing and stable region segmentation for each particle image can be performed even for a urine specimen in which urine particles having different tones coexist.

Still furthermore, an apparatus for region segmentation of a urine particle image is characterized by comprising: a means for extracting a first object region by using one or more of an R image, a G image, and a B image of a urine particle image taken by an image input optical system configured to input particle images; a means for calculating a density distribution of the one or more of the R image, the G image, and the B image in the first object region and a size of the first object region, and classifying the first object region into a predetermined number of groups based on the density distribution and the size; and a means for extracting a second object region from a local region including the first object region in the image by using one or more of the R image, the G image, and the B image, depending on each of the groups.

Effects of the Invention

With the method for region segmentation of urine particle images according to the present invention, stable region segmentation can be performed for each particle image even for a urine specimen in which urine particles having different sizes and tones coexist and thus a more accurate binary image can be obtained. This effect consequently allows accurate calculation of feature parameters of an object region, prevention of erroneous classification of an object particle, and therefore improvement of accuracy in identifying urine particles of various types.

DESCRIPTION OF SYMBOLS 101 example of urine particle image
102 example of first object region
103 example of grouping
104 example of second object region
201 apparatus
202 stainer unit
203 input unit
204 display
205 keyboard
206 processing unit
301 flow cell
302 pulse lamp
303 objective lens
304 camera
701 example of urine particle image
702 example of object particle
703 example of first object region
704 example of local region rectangle including first object region
1301 discriminating boarder
1302 discriminating boarder
1303 symbols belonging to Group A
1304 symbols belonging to Group B 1305 symbols belonging to Group C
1306 symbols belonging to Group D

BEST MODES FOR CARRYING OUT THE INVENTION

Embodiments of the present invention will be described below with reference to the drawings.

Embodiment 1

Figure 2:
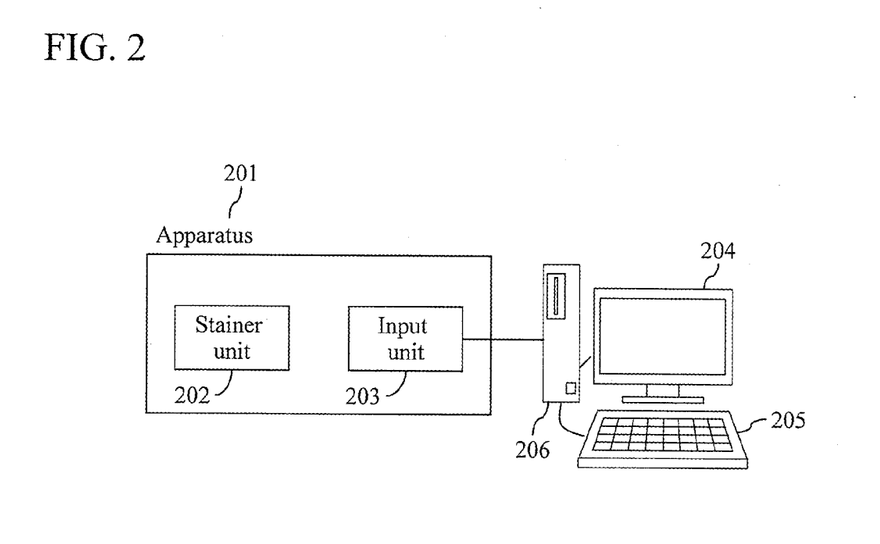
FIG. 2 is a diagram illustrating a configuration example of the urine sediment examination apparatus.

FIG. 2 is a diagram illustrating an apparatus for automatic analysis of urinary sediments, to which the present invention is applied. In an apparatus 201, a stainer unit 202 stains a urine specimen with a stain, and after a certain period of time, an input unit 203 takes an enlarged static image of particles in the urine. The image thus taken is transferred to a processing unit 206, where the urine particles are classified through image pattern recognition. The processing unit 206 then counts the types of the urine particles included in a single specimen as well as the appearance frequency of each type. For example, a general-purpose personal computer having a display 204 and a keyboard 205 is used as the processing unit 206. The operator is informed of the counting results through the display 204. The image taken by the input unit 203, data obtained by the processing unit 206, such as a measurement result, a classification result for each object region, and image feature parameters obtained during the image pattern recognition, are saved in a storage device in the processing unit 206. The processing unit 206 also has a review function which allows the operator to display any selected image and to make a correction to the automatic classification or to perform fine classification visually.

Figure 3:
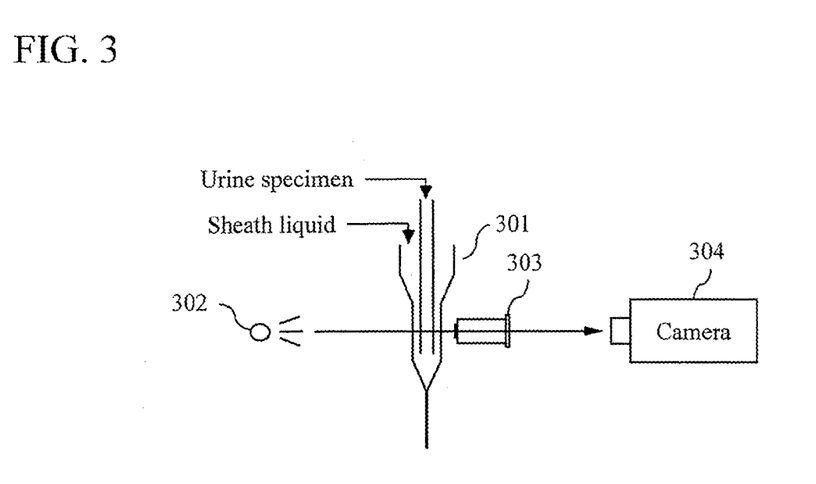
FIG. 3 is a diagram illustrating a configuration example of an input unit of the urine sediment examination apparatus.

FIG. 3 is a schematic diagram of the input unit 203 of the apparatus 201. In the input unit 203, a flow cell 301 is used to form a wide, flat and thin flow for urine specimen between an objective lens 303 and a pulse lamp 302. While the flow for urine specimen formed by the flow cell 301 is irradiated by the pulse lamp 302 momentarily, an image of urine particles enlarged by the objective lens 303 is taken by a camera 304 as a static image. As the camera 304, a CCD color camera, a CMOS color camera, or the like is used for example. The image thus obtained is transferred to the processing unit 206.

Figure 4:
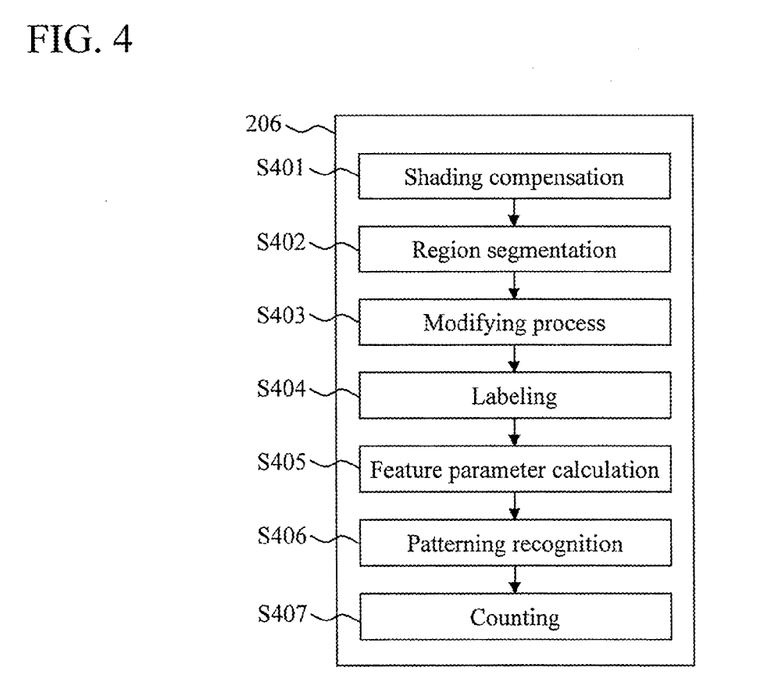
FIG. 4 is a diagram illustrating an image processing method by the urine sediment examination apparatus.

FIG. 4 is a diagram illustrating how the processing unit 206 performs image processing. An image of urine particles taken by the camera 304 is transferred to the processing unit 206 as digital data. In shading compensation step S401, density unevenness of the image, resulting from the characteristics of the optical system, is removed.

In region segmentation step S402, a binary image is formed by segmenting the image of urine particles into a background region and an object region. In the binary image, 0 indicates the background region, and 1 indicates the object region. In modifying process step S403, correction and shaping of the binary image is performed, such as compensation for the object region and noise removal for the background region. A known conventional technique, including filtering processing such as, for example, swelling and shaping, can be used as the means for the correction and shaping.

In labeling step S404, each group of connected components in the binary image is labeled and assigned a number to be uniquely identified among multiple objects in the image. In feature parameter calculation step S405, feature parameters, such as an area, a perimeter, and an average density value, are calculated for each object region thus numbered.

In patterning recognition step S406, each object region is classified on the basis of its component type by using the image parameters obtained for the object region in step S405. As the means for the patterning recognition, a neutral network approach, a statistical recognition approach, or the like can be used. Examples of items used for the classification include a red blood cell, a white blood cell, a squamous epithelial cell, other epithelial cells, a cast, a crystal, a bacterium, and the like.

In counting step S407, based on the classification results obtained in patterning recognition step S406, the objects classified into each classification class are counted. The counting results are converted into the number of objects or the density per unit volume of the urine specimen, and the conversion results are outputted to the display 204.

Note that all or part of the processing shown in FIG. 4 can also be processed by hardware.

Figure 5:
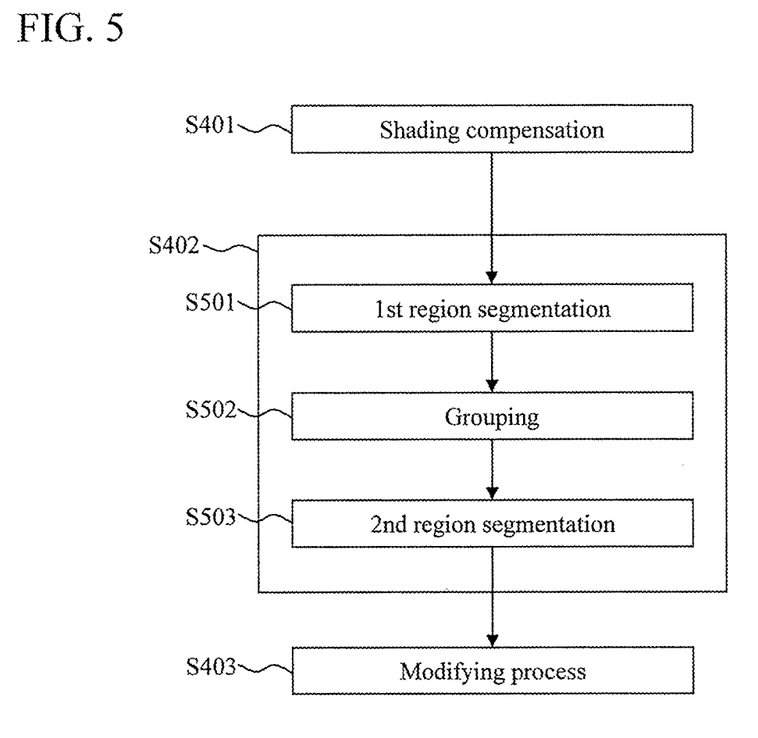
FIG. 5 is a detailed configuration example of the region segmentation.

FIG. 5 is a diagram illustrating in detail a configuration example of region segmentation step S402.

Figure 1:
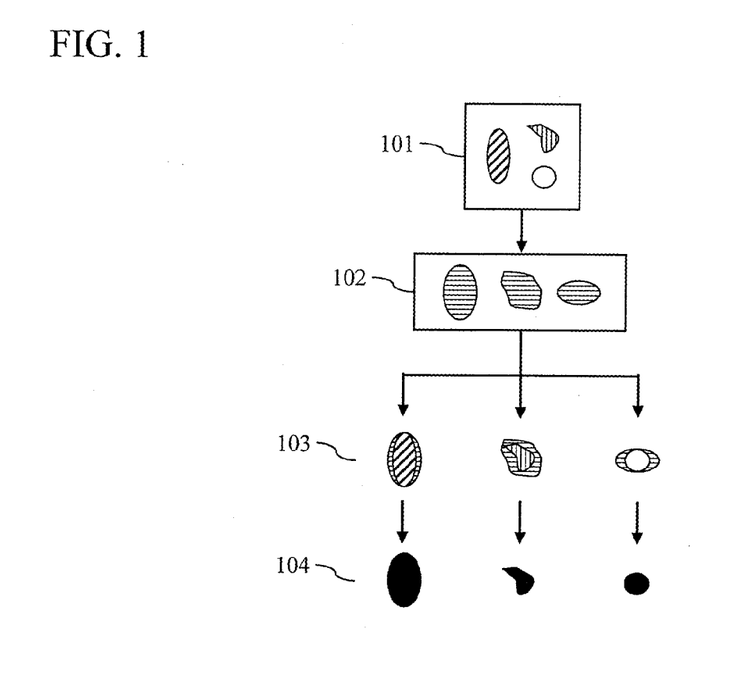
FIG. 1 is a diagram showing a configuration example of region segmentation by a urine sediment examination apparatus to which the present invention is applied.

In step S501, first object regions in each of which an object particle exist are extracted from an image of urine particles. A region larger than the object particle is extracted by the segmentation here so that the object particle including a hard-to-stain particle can be extracted as one continuous region. For example, suppose that an image 101 of urine particles shown in FIG. 1 is taken by an input optical system configured to input particle images. Then, the region segmentation is carried out using one or more of an R image, a G image, and a B image of the image 101 and using a fixed threshold predetermined by experiment, or the like. As a result, regions larger than the object particles are obtained as the region segmentation results, as shown in 102 of FIG. 1.

In step S502, each first object region is grouped into a predetermined number of groups. Feature parameters of the first object region are used for the grouping. The feature parameters used here include a feature parameter for size and a feature parameter for tone. For example, an area, a perimeter, or the like is used for the feature parameter for size. For example, an average density value or the like is used for the feature parameter for tone. As an example, in FIG. 1, the first object region is grouped into three groups based on the tone and the size thereof, and 103 of FIG. 1 shows the grouping results.

In step S503, second object regions are extracted from respective local regions each including the first object region by carrying out group-specific region segmentation. For example, the region segmentation here employs a method which uses one or more of an R image, a G image, and a B image of the image of urine particles and a fixed threshold predetermined by experiment, or employs other methods. The type and the number of the images selected and the fixed threshold used are different for each group. For example, in a case of urine particles stained with a typical Sternheimer(S) stain, the absorption peak of the particles stained is on the order of 550 nm. Accordingly, higher sensitivity can be obtained by using a G image or a R image having a 500 to 700 nm wavelength than by using a B image having a 400 to 500 nm wavelength. Further, the particles stained include stained particles that are sufficiently stained and light-stained particles that are insufficiently stained. In such a case, the same image may be used, but the fixed threshold has to be changed according to the tone. Moreover, for the region segmentation, a contour extraction method, such as dynamic contour (snake), which is a known conventional technique may be used. For example, 104 of FIG. 1 shows results of object regions accurately extracted as a result of the region segmentation performed differently for each group.

As described above, a first object region larger than a particle image is extracted. Then, the first object region is classified into a predetermined number of groups based on the tone and the size thereof. Based on the classification result, a second object region is extracted according to the features of the particle image. This configuration offers such an effect that stable region segmentation can be performed for each particle image even for a urine specimen in which urine particles having different sizes and tones coexist.

Figure 6:
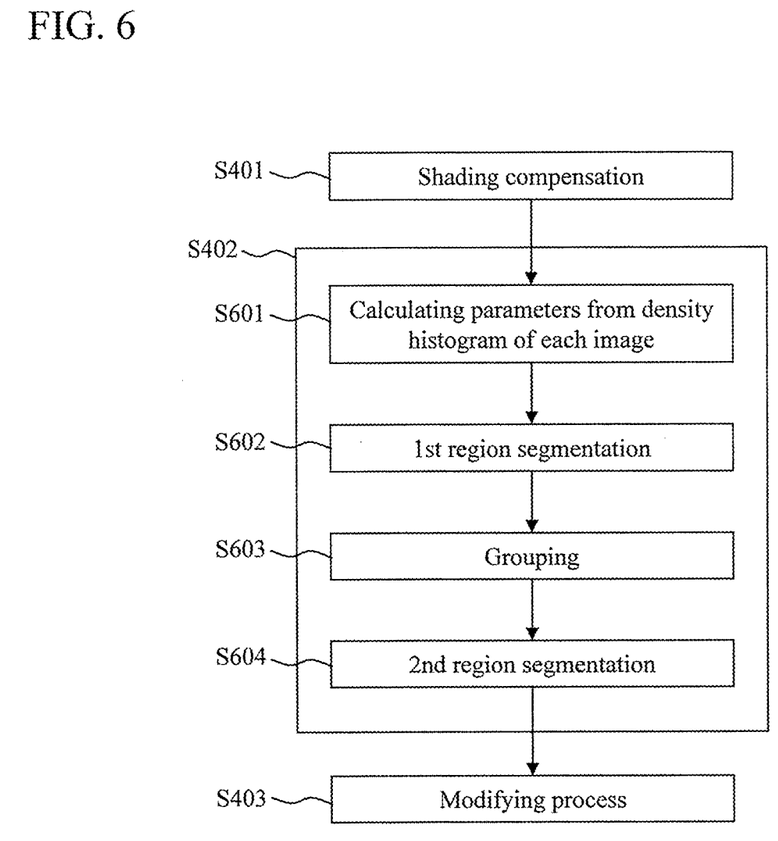
FIG. 6 is a diagram illustrating a detailed configuration in a case of using a density histogram of each image for the region segmentation.

FIG. 6 is a diagram illustrating a detailed configuration employed in a case where a density histogram of each of an R density, a G density, and a B density of a urine particle image is used in region segmentation step S402.

Figure 7:
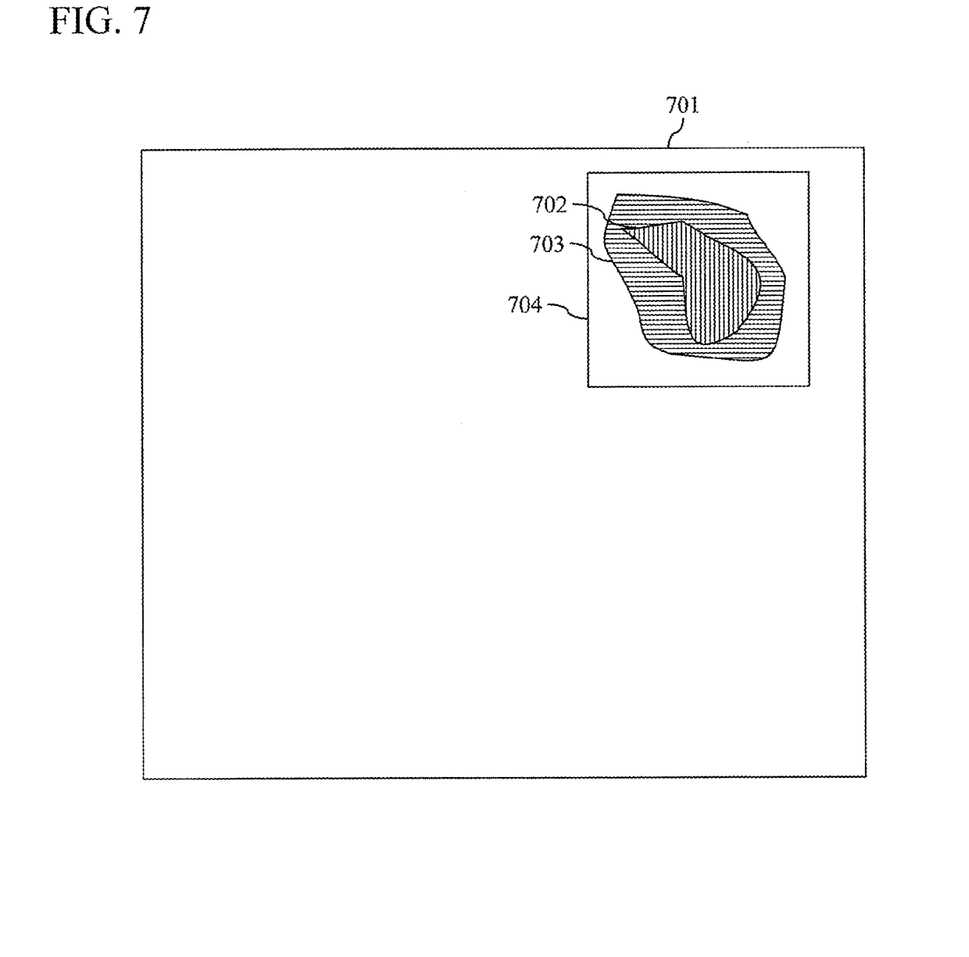
FIG. 7 is a diagram showing an example of a urine particle image obtained by the urine sediment examination apparatus.

In step S601, a density histogram is created for each of the R density, the G density, and the B density of the urine particle image, and for each density histogram, parameters indicating the shape thereof are obtained. In step S602, a first object region in which an object particle exists is extracted from the image by using the parameters obtained in step S601 and the like. A region larger than the object particle is extracted by the segmentation here so that the object particle including a hard-to-stain particle can be extracted as one continuous region. For example, when a urine particle image 701 shown in FIG. 7 is obtained, the first object region obtained in step S602 is a region 703 being larger than an object particle 702.

In grouping step S603 of FIG. 6, the first object region is grouped into a predetermined number of groups, based on its average density value distribution and size. Note that an area, a perimeter, or the like is used as the size. In second region segmentation step S604, a second object region representing a more accurate shape of the object particle is extracted from a local region including the first object region using an optimum region segmentation method which is different for each group. The second object region thus extracted is subjected to a modifying process in step S403.

Figure 8:
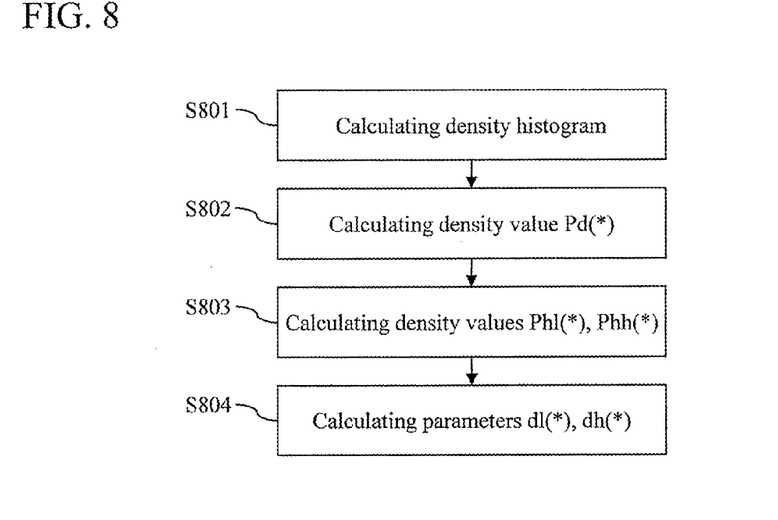
FIG. 8 is a diagram illustrating a detailed procedure for obtaining parameters indicating the shape of the density histogram of each image.

FIG. 8 shows a detailed procedure, conducted in step S601 of FIG. 6, for obtaining parameters Pd(*), Phl(*), Phh(*), dl(*), and dh(*) indicating the shape of the density histogram of each image. Note that * indicates any one of R, G, and B.

Figure 9:
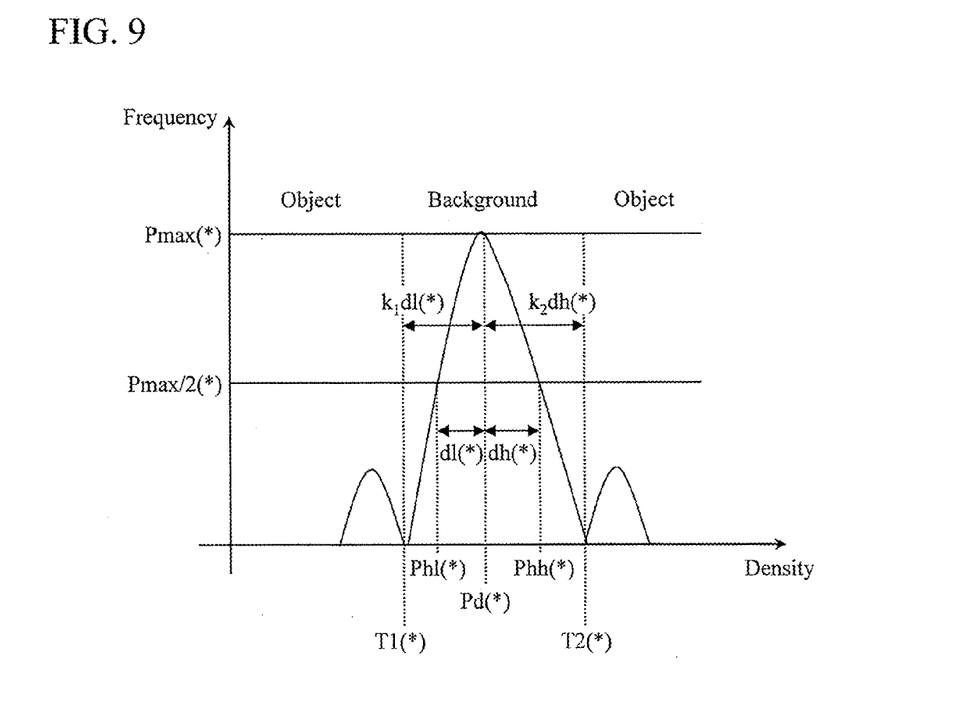
FIG. 9 shows an example of the density histogram.

In step S801, a density histogram is created for each of the R image, the G image, and the B image. In step S802, as shown in FIG. 9, a density value Pd(*) having a maximum frequency value Pmax(*) is obtained for each density histogram. Note that * indicates any one of R, G, and B. In step S803 of FIG. 8, as shown in FIG. 9, density values Phl(*) and Phh(*) having a value Pmax/2(*) which is a half width of the peak are obtained for each density histogram. Note that * indicates any one of R, G, and B. Although density values having the half value of the peak are used here, the density values are not limited to such values, and may be ones having a quarter, a tenth, or the like of the peak, instead. Optimum density values should be decided from the shape of the histogram. In step S804 of FIG. 8, dl(*) and dh(*) in FIG. 9 are calculated through Formulae (1) and (2) shown below using Pd(*) in FIG. 9 obtained in step S802 and Phl(*) and Phh(*) in FIG. 9 obtained in step S803. Note that * indicates any one of R, G, and B.

$$dl(*)=Pd(*)-Phl(*) \tag{1}$$

$$dh(*)=Phh(*)-Pd(*) \tag{2}$$

Figure 10:
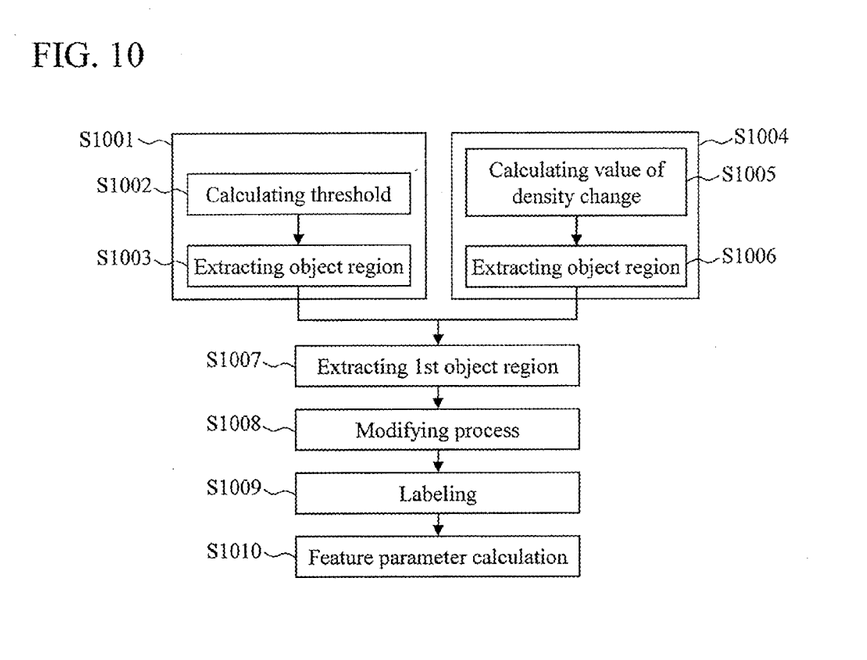
FIG. 10 is a diagram showing a detailed procedure for first region segmentation in which a region larger than an object is extracted.

FIG. 10 shows a detailed procedure for the first region segmentation, conducted in step S602 of FIG. 6, in which a region larger than an object is extracted.

First, step S1001 shows a procedure for extracting an object region by using the density histogram. In step S1002, thresholds T1(*) and T2(*) shown in FIG. 9 are calculated through Formulae (3) and (4) shown below using Pd(*) obtained in step S802 of FIG. 8 and dl(*) and dh(*) obtained in step S804 of FIG. 8. Note that * indicates any one of R, G, and B.

$$T1(*)=Pd(*)-dl(*) \times k_1(*) \tag{3}$$

$$T2(*)=Pd(*)+dh(*) \times k_2(*) \tag{4}$$

$k_1(*)$ and $k_2(*)$ are coefficients predetermined by experiment, and optimum coefficients which are different for each of the R image, the G image, and the B image are obtained in advance. Note that one or more of density values that have the highest sensitivity due to the color characteristics of the urine particles and spectral characteristics of the camera are selected and used for the calculation of thresholds.

For example, if the R image and the G image are selected, the threshold values are calculated as follows.

$$T1(R)=Pd(R)-dl(R) \times k_1(R)$$

$$T2(R)=Pd(R)+dh(R) \times k_2(R)$$

$$T1(G)=Pd(G)-dl(G) \times k_1(G)$$

$$T2(G)=Pd(G)+dh(G) \times k_2(G)$$

$k_1(R)$, $k_2(R)$, $k_1(G)$, and $k_2(G)$ are coefficients predetermined by experiment, and optimum coefficients which are different for each image are obtained in advance.

In step S1003, an object region is extracted using the thresholds thus obtained. For example, if the thresholds T1(R), T2(R), T1(G), and T2(G) are used, pixels (x, y) satisfying Formula (5) shown below are extracted as the object region.

$$\{T1(R) \geq R(x,y)\} II \{T2(R)<R(x,y)\} II \{T1(G) \geq G(x,y)\} II \{T2(G)<G(x,y)\} \tag{5}$$

Here, II indicates a logical OR. R(x, y) indicates an R density value of the pixel (x, y), and G(x, y) indicates a G density value of the pixel (x, y).

Since a region larger than the object particle is to be extracted as the first object region in step S602 of FIG. 6, the coefficient $k_n(*)$ is set to be somewhat small. Setting the coefficient $k_n(*)$ small increases the area of the object region in FIG. 9.

Next, step S1004 shows a procedure for extracting an object region by using the magnitude of density value change. In step S1005, a value indicating the magnitude of density value change is calculated.

Here, as the index of the magnitude of density value change, a difference between density values in a local small region is used. In step S1005, when the difference between density values in a local small region is used, a density difference value defined by Formula (6) shown below is used. r(*)(x, y) is obtained by:

$$r(*)(x, y) = \sum_{i=1}^{n} (*(x, y)_{+i} - *(x, y)_{-i}) \tag{6}$$

where *(x, y) and r(*)(x, y) indicate a density value and a density difference value, respectively, at the pixel position (x, y) on the image.

Note that * indicates any one of R, G, and B.

In step S1006, using r(*)(x, y), pixels (x, y) satisfying Formula (7) shown below are extracted as an object region.

$$s_n(*) \leq |r(*)(x,y)| \tag{7}$$

Here, || indicates that a value therebetween is an absolute value, and $s_n(*)$ is a constant predetermined by experiment, and an optimum constant different for each color is obtained in advance. Note that * indicates any one of R, G, and B.

The number of neighboring pixels used for calculating a difference value for a given pixel is represented by 2n+1, and is called a mask size. When n=2 for example, two pixels before and after the given pixel in an x direction or in a y direction are needed for the calculation of a difference value for the given pixel, and therefore the mask size=5. A mask size of 1 means that no difference processing is performed.

Note that one or more images having the highest sensitivity due to the color characteristics of the urine particles and spectral characteristics of the camera are used for the region segmentation. In addition, the mask size in each of the x direction and the y direction is set as large as possible within an object region of a nonstained particle.

Suppose, for example, that the G image is selected and that the mask size in the x direction is 5, and the mask size in the y direction is 1. In this case, pixels (x, y) satisfying Formula (8) shown below are extracted as the object region.

$$r(G)(x,y)=G(x+2,y)+G(x+1,y)-G(x-2,y)-G(x-1,y)s1$$
$$(G) \le |r(G)(x,y)| \quad (8)$$

| | indicates that a value therebetween is an absolute value, and s1(G) is a constant for which an optimal value is predetermined by experiment.

Note that the index of the magnitude of density value change is not limited to the density value difference. Other methods may be used, including a method using a density value distribution in a local small region, a method using filtering processing for emphasizing frequency components specifically included in the object region, and the like.

In step S1007, a first object region is extracted by superimposing (i.e., logically ORing) the object regions obtained in step S1001 and step S1004, respectively. Suppose, for example, that the object region extraction in step S1001 uses the R image and the G image and uses Formula (5) and that the object region extraction in step S1004 uses the G image with a combination of a mask size of 5 in the x direction and a mask size of 1 in the y direction and uses Formula (8). Then, pixels (x, y) satisfying the following formula are obtained as the first object region. Here, II indicates a logical OR.

$$\{T1(R) \ge R(x,y)\}II\{T2(R)<R(x,y)\}II\{T1(G) \ge G(x,y)\}II\{T2(G)<G(x,y)\}IIs1(G) \le |r(G)(x,y)|$$

In step S1008, the first object region extracted is subjected to a modifying process in such a manner similar to step S403 of FIG. 4. In step S1009, the first object region is subjected to labeling in such a manner similar to step S404 of FIG. 4. In step S1010, feature parameters, such as an area, a perimeter, and an average density value, are calculated for the first object region thus numbered. The feature parameters thus calculated are used in the grouping in step S603 of FIG. 6.

Figure 11:
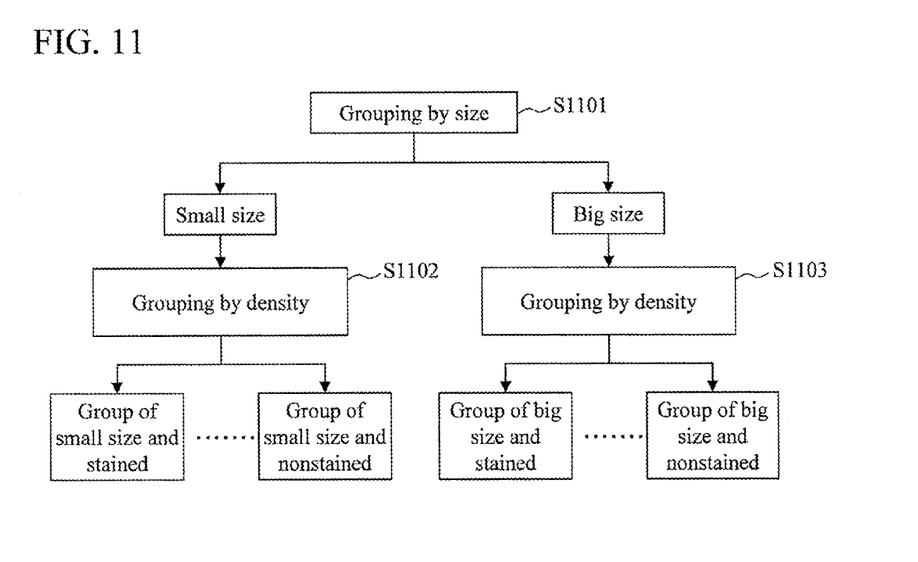
FIG. 11 is a diagram showing a detailed procedure for grouping the first object region.

FIG. 11 shows a detailed procedure for the grouping performed in step S603 of FIG. 6. In step S1101, based on the feature parameter for size of the first object region, the first object region is classified into two groups: a group of big size particles and a group of small size particles. An area, a perimeter, or the like is used for the feature parameter for size.

Figure 12:
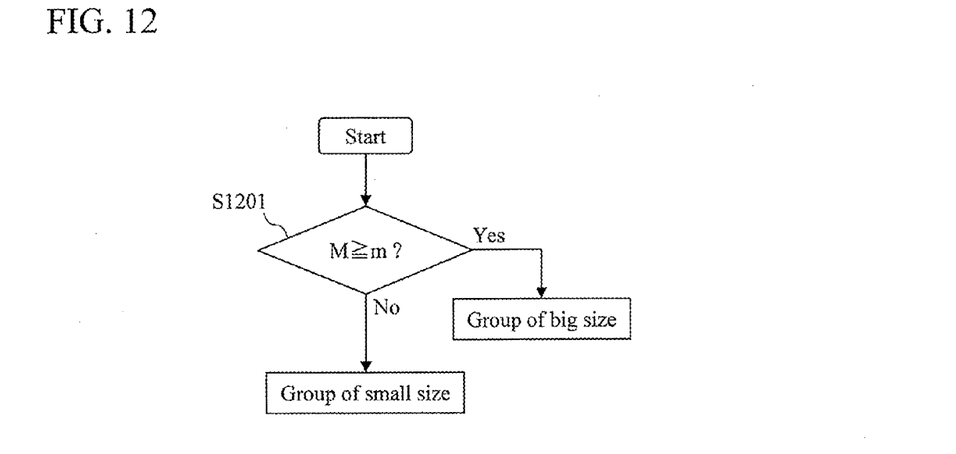
FIG. 12 is a diagram illustrating a flow of an example of the grouping carried out when an area is used as the parameter for size.

FIG. 12 is a diagram illustrating a flow of the grouping performed using an area as the feature parameter for size. In a determination in step S1201, the first object region satisfying $M \ge m$ is classified as a group of big size particles, and the first object region not satisfying $M \ge m$ is classified as a group of small size particles. Here, M is the area of the first object region, and m is an optimum value obtained in advance by experiment.

In step S1102 of FIG. 11, using the average density value of the first object region, the first object region is grouped into a predetermined number of groups according to the tone thereof. For the average density value, one or more of color images having the highest sensitivity due to the color characteristics of the object region and the spectra characteristics of the camera are selected. The first object region is grouped into the predetermined number of groups, depending on where in the density space the average density value of the image thus selected is located. Here, discriminating boarders used for the grouping in the density space are predetermined by experiment. For example, the discriminating boarders can be obtained using a known conventional technique such as discriminant analysis.

Figure 13:
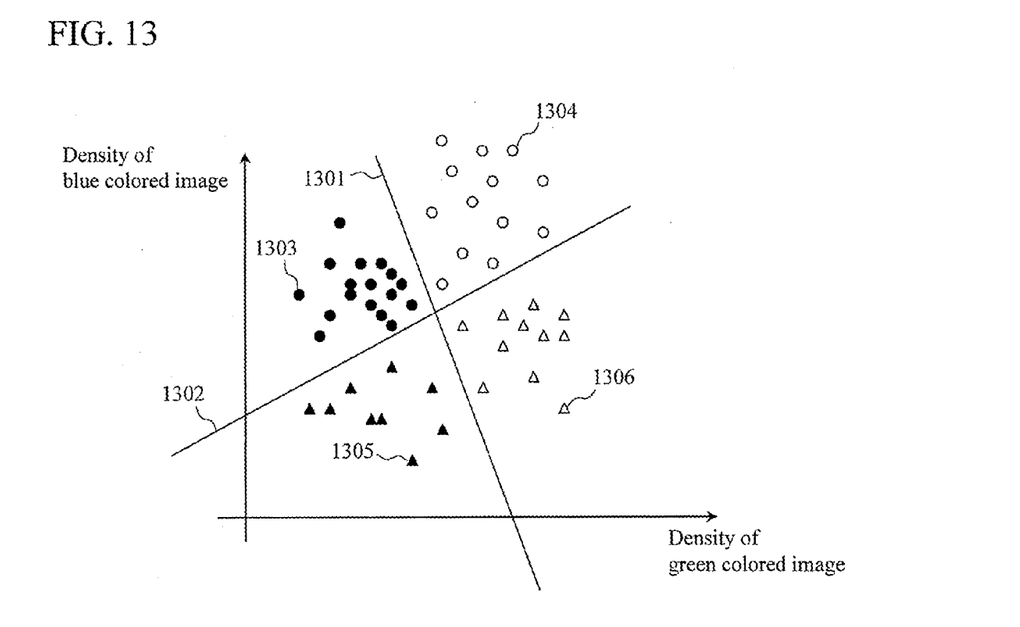
FIG. 13 is a diagram illustrating an example of a distribution chart used when a G density and a B density are selected for density values used for the grouping.

FIG. 13 is a diagram illustrating an example of a distribution chart used in the grouping when, for example, the G density and the B density are used for the density values. Symbols 1303 to 1306 indicate coordinates (g, b) of the average density values of the urine particles collected in advance to form a distribution chart. It has been made clear by experiment that an optimum region segmentation method is different for each group of the urine particles collected. Here, the urine particles are grouped into four groups, A, B, C and D, according to the tone thereof, and the symbols 1303 to 1306 represent distributions, in a G-B space, of particles belonging to the groups A, B, C, and D, respectively. Discriminating boarders 1301 and 1302 are calculated using, for example, linear discriminant analysis. The linear discriminant analysis uses density value data on the symbols. The discriminating boarders thus calculated can be represented by the following formulae.

$$b=j_1g+k_1 \text{ (discriminating boarder 1301)}$$

$$b=j_2g+k_2 \text{ (discriminating boarder 1302)}$$

Figure 14:
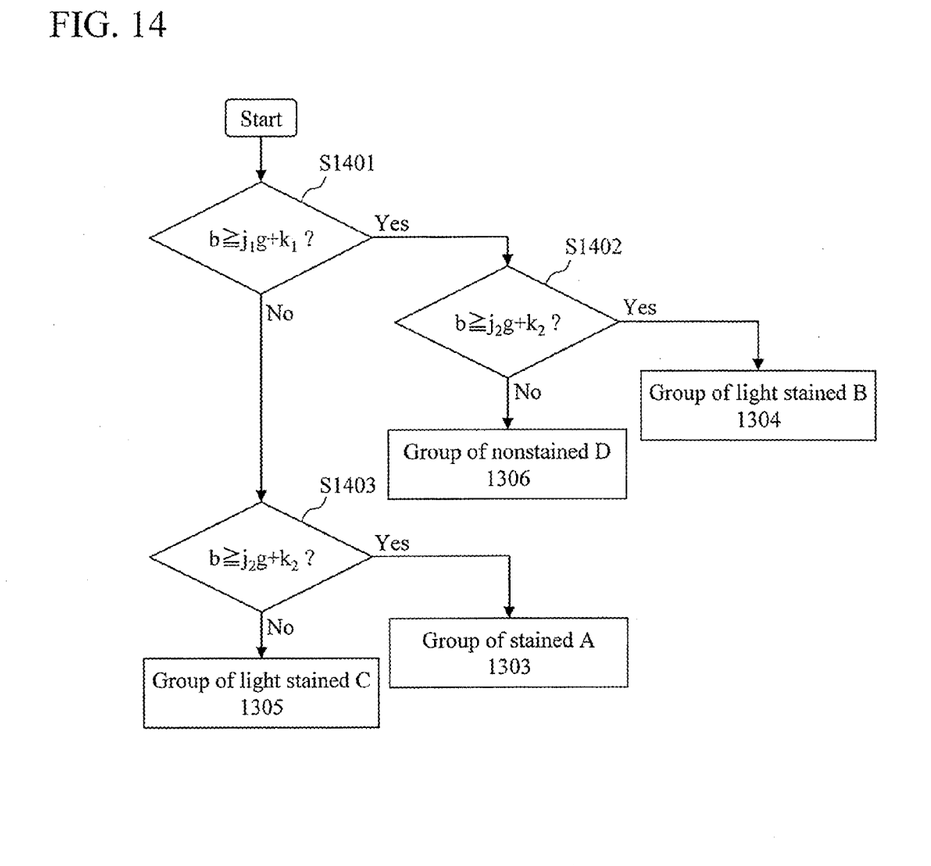
FIG. 14 is a diagram illustrating a flow of an example of grouping carried out when a G-B distribution chart is used as the density values used for the grouping.

FIG. 14 is a diagram illustrating a flow of grouping performed when the G-B distribution chart in FIG. 13 is used in the grouping in step S1102 of FIG. 11.

When the average density value of the G image and the B image of a certain first object region is represented as (g, b), the first object region belongs to a group of light-stained B (1304) if $b \ge j_1 g + k_1$ is satisfied in a determination in step S1401 and additionally if $b \ge j_2 g + k_2$ is satisfied in step S1402. The first object region belongs to a group of nonstained D (1306) if $b \ge j_1 g + k_1$ is satisfied in the determination in step S1401 and additionally if $b \ge j_2 g + k_2$ is not satisfied in step S1402.

The first object region belongs to a group of stained A (1303) if $b \ge j_1 g + k_1$ is not satisfied in the determination in step S1401 and additionally if $b \ge j_2 g + k_2$ is satisfied in step S1402. The first object region belongs to a group of light-stained C (1305) if $b \ge j_1 g + k_1$ is not satisfied in the determination in step S1401 and additionally if $b \ge j_2 g + k_2$ is not satisfied in step S1402.

In step S1103 of FIG. 11, the grouping is performed in a similar manner to step S1102. Note that the number of classification groups and the classification method used in step S1103 are predetermined by experiment and are different from those used in S1102.

Figure 15:
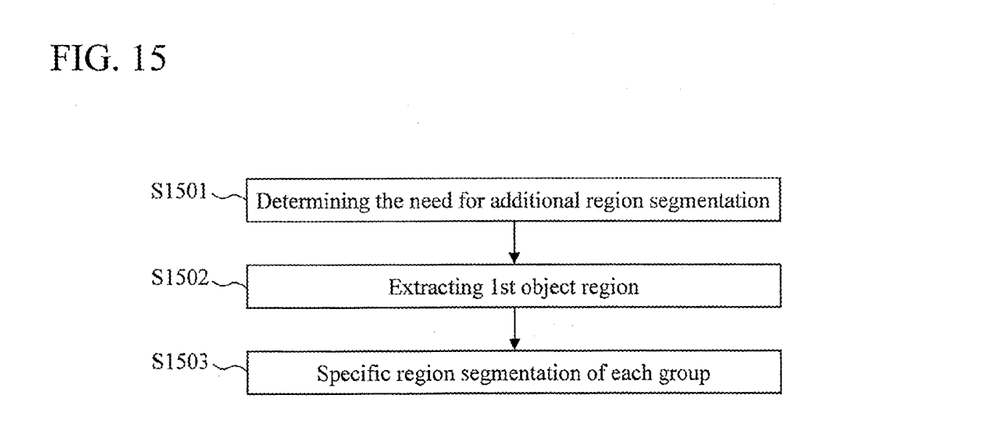
FIG. 15 is a diagram showing a detailed procedure for group-specific second region segmentation.

FIG. 15 shows a detailed procedure for the group-specific second region segmentation performed in step S604 of FIG. 6.

Figure 16:
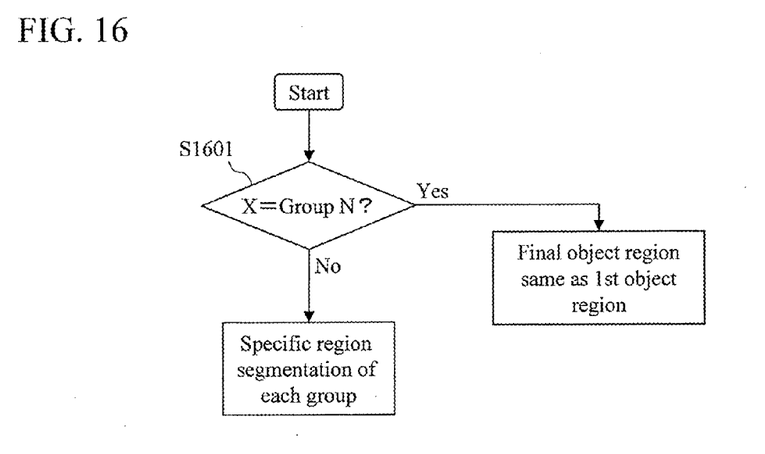
FIG. 16 is a diagram illustrating a flow of an example of processing for determining the need for additional region segmentation for each group.

In step S1501, the need for additional region segmentation is determined for each group. FIG. 16 shows a detailed flow of step S1501. For example, assume that Group N is predetermined by experiment as not needing additional region segmentation. For example, if Group X to which a certain first object region x belongs satisfies X=N in step S1601, the first object region x does not need additional region segmentation and is determined as the final result of region segmentation. If X=N is not satisfied in step S1601, the first object region x needs additional region segmentation, and the flow proceeds to step S1502.

For example, Group N is big size particles. In a case of big size particles, because an object is big in the first place, the region segmentation in step S602 of FIG. 6 of extracting an object with a larger region does not give much difference to the feature parameters calculated in step S405 of FIG. 4. Accordingly, the patterning recognition in S406 of FIG. 4 is performed with no problem, making final classification of urine particles unlikely to be erroneous. In addition, not needing additional region segmentation saves the time for the region segmentation, and therefore offers an effect of improving a processing speed of image processing.

In step S1502 of FIG. 15, a local region including the first object region is extracted. As the local region, a local rectangle including the first object region is extracted. For example, if the urine particle image 701 shown in FIG. 7 is obtained, a rectangle 704 including the first object region 703 obtained in step S602 of FIG. 6 is extracted as the local region.

In step S1503, group-specific region segmentation, which is different for each group, is performed to extract a more accurate second object region from the local region including the first object region.

Figure 17:
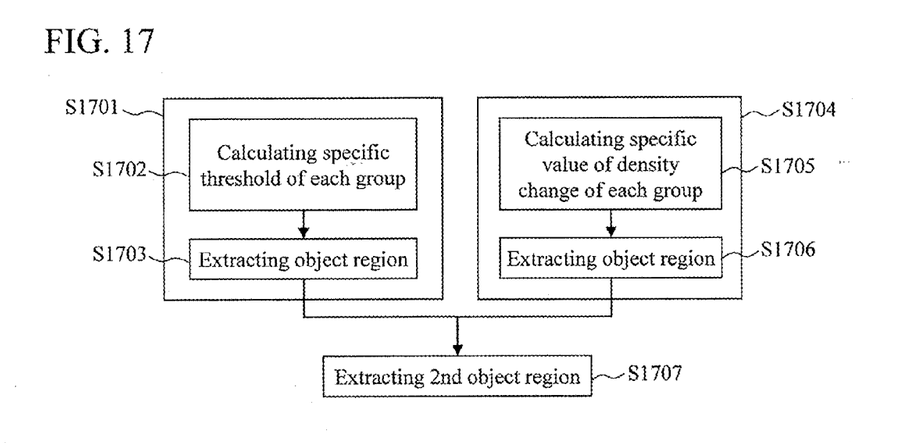
FIG. 17 is a diagram showing a detailed procedure for the group-specific second region segmentation.

FIG. 17 shows a detailed procedure for the second region segmentation performed in step S1503. Step S1701 is basically the same as step S1001 of FIG. 10, but the color images and parameters used in step S1702 are different for each group. In addition, the coefficient $k_n(*)$ used in the threshold calculation is different for each group, so that the thresholds are calculated differently for each group. Note that * indicates any one of R, G, and B.

Step S1704 is basically the same as step S1004 of FIG. 10, but the color images, the constant $s_n(*)$, and the mask sizes used in step S1705 are different for each group. Note that * indicates any one of R, G, and B.

In step S1707, a second object region, which is extracted in step S604 in the flow of FIG. 6, is extracted. The second object region is obtained by superimposing (logically ORing) the object regions obtained in step S1703 and step S1706, respectively. For example, assume that there are three groups obtained in advance by experiment: a group of stained particles (1), a group of light-stained particles (2), and a group of nonstatined particles (3).

Suppose that a certain first object region belongs to the group of stained particles (1), and that the object region extraction in step S1701 uses the R image and the G image, and the object region extraction in step S1704 uses the G image with a combination of a mask size of 5 in the x direction and a mask size of 1 in the y direction. Then, the second object region is obtained by the following formula.

$$\{T3(R) \geq R(x,y)\} \textit{II} \{T4(R) < R(x,y)\} \textit{II} \{T3(G) > G(x,y)\} \textit{II} \{T4(G) < G(x,y)\} \textit{IIs2}(G) \leq |r(G)(x,y)|$$

Suppose that a certain first object region belongs to the group of light-stained particles (2), and that the object region extraction in step S1701 uses the R image and the G image, and the object region extraction in step S1704 uses a mask size of 1 in both the x and y directions. Then, the second object region is obtained by the following formula.

$$\{T5(R) \geq R(x,y)\} \textit{II} \{T6(R) < R(x,y)\} \textit{II} \{T5(G) \geq G(x,y)\} \textit{II} \{T6(G) < G(x,y)\}$$

Suppose that a certain first object region belongs to the group of nonstained particles (3), and that the object region extraction in step S1701 uses the B image, and the object region extraction in step S1704 uses a mask size of 1 in both the x and y directions. Then, the second object region is obtained by the following formula.

$$\{T1(B) \geq B(x,yj)\} \textit{II} \{T2(B) < B(x,y)\}$$

The region segmentation method of the present invention in which threshold processing is performed using density histograms offers such an effect that stable threshold processing can be performed even for a urine specimen in which urine particles having different tones coexist.

In the present invention, a first object region larger than a particle image is extracted. Then, the first object region is classified into a predetermined number of groups based on the tone and the size thereof. Based on the classification result, a second object region is extracted according to the features of the particle image. This configuration of the present invention offers such an effect that stable region segmentation can be performed for each particle image even for a urine specimen in which urine particles having different sizes and tones coexist. This effect consequently allows accurate calculation of feature parameters of an object region, prevention of erroneous classification of an object particle, and therefore improvement of accuracy in identifying urine particles of various types.

Embodiment 2

Figure 18:
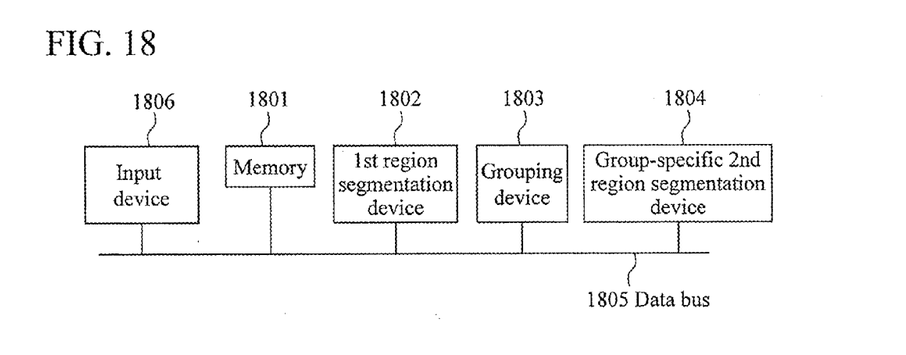
FIG. 18 is a diagram illustrating a configuration of an apparatus for region segmentation of urine particle images, according to a second embodiment of the present invention.

FIG. 18 is a diagram illustrating the configuration of an apparatus for region segmentation of urine particle images according to a second embodiment of the present invention.

An original image taken by an input device, such as a camera, is transferred to a memory 1801. The original data is then transferred to a first region segmentation device 1802, where first region segmentation is carried out. For the first region segmentation, the method described in Embodiment 1 may be used. Images of first object regions obtained through the region segmentation are transferred to the memory 1801.

Next, the first object regions are transferred to a grouping device 1803, where feature parameters are calculated for each first object region, and the first object region is classified into a predetermined number of groups. For the grouping, the method described in Embodiment 1 may be used. Results of the grouping are transferred to the memory 1801.

A group-specific second region segmentation device 1804 performs region segmentation using the original image, the first object regions, and the grouping results that are saved in the memory 1801, and thereby obtains second object regions each accurately representing the shape of an object particle. For the detail group-specific region segmentation, the method described in Embodiment 1 may be used. Results of the second object regions are transferred to the memory 1801. Note that the means for saving the results of the second region segmentation is not limited to the memory 1801, and may be, for example, an external storage medium such as an HDD or a floppy disk.

In the configuration of the apparatus of the present invention, a first object region larger than a particle image is extracted, and is classified into a predetermined number of groups based on the tone and the size of the first object region, and the second object region is extracted based on the classification result and the features of the particle image. This configuration offers such an effect that stable region segmentation for each particle image can be carried out even for a urine specimen in which urine particles having different sizes and tones coexist.

The invention claimed is:

1. A method for region segmentation of urine particle images, comprising the steps of:
    extracting a first object region larger than an object particle included therein, from a urine particle image taken by an image input optical system, by using at least one of an image with red components of the urine particle image (an R image), an image with green components of the urine particle image (a G image), and an image with blue components of the urine particle image (a B image);
    calculating a size of the first object region based on at least one of an area or a perimeter of the first object region and a density distribution of the first object region, in the first object region, of each of the at least one of the R image, the G image, and the B image, and classifying the first object region into one group of a predetermined number of groups, based on the size of the first object region and the density distribution of the first object region; and
    extracting a second object region, representing the object particle, from the first object region, by using group-specific region segmentation, which includes use of the at least one of the R image, the G image, and the B image.

2. A method for region segmentation of urine particle images, comprising:
    first step of creating a density histogram of each of a red (R) density of a urine particle image taken by an image input optical system, a green (G) density of the urine particle image taken by the image input optical system, and a blue (B) density of the urine particle image taken by the image input optical system, by using a red (R) image, a green (G) image, and a blue (B) image of the urine particle image taken by the image input optical system, and thereby obtaining at least one parameter indicating a shape of the density histogram;
    a second step of extracting a first object region larger than an object particle included therein, from the urine particle image, by using the at least one parameter, and at least one of the R image, the G image, and the B image;
    a third step of calculating a size of the first object region based on at least one of an area or a perimeter of the first object region and a density distribution of the first object region, in the first object region, of each of the at least one of the R image, the G image, and the B image, and of classifying the first object region into a one group of a predetermined number of groups, based on the size of the first object region, and the density distribution of the first object region; and
    a fourth step of extracting a second object region, representing the object particle, from the first object region, by using group-specific region segmentation, including use of the at least one parameter, and the at least one of the R image, the G image, and the B image.

3. The method for region segmentation of urine particle images according to claim 2, characterized in that the second step includes the steps of:
    calculating a density threshold of each of at least one of the R image, the G image, and the B image, based on the at least one parameter obtained in the first step; and
    extracting an object region, by applying the density threshold to each of the images.

4. The method for region segmentation of urine particle images according to claim 2, characterized in that the second step includes the steps of:
    obtaining values, by performing filtering processing on the at least one of the R image, the G image, and the B image; and
    extracting an object region, by performing threshold processing on the values.

5. The method for region segmentation of urine particle images according to claim 2,
    wherein in the second step, a region is extracted as the first object region, by performing a logical OR operation on the following values:
    a region segmentation result extracted through region segmentation, by calculating a density threshold of each of the at least one of the R image, the G image, and the B image, from the at least one parameter obtained in the first step, and by applying the threshold to each of the images, and
    a region segmentation result extracted through region segmentation by performing threshold processing on values obtained, by performing filtering processing on the at least one of the R image, the G image, and the B image.

6. The method for region segmentation of urine particle images according to claim 2, characterized in that the fourth step includes the steps of:
    selecting at least one of the R image, the G image, and the B image, for each of the groups specified in the third step;
    calculating a threshold for each of the selected color images by using the at least one parameter obtained in the first step; and
    performing region segmentation for each of the groups by using the threshold.

7. The method for region segmentation of urine particle images according to claim 2, characterized in that the fourth step includes the steps of:
    selecting at least one of the R image, the G image, and the B image, for each of the groups specified in the third step;
    calculating a threshold for each of the selected color images by using the at least one parameter obtained in the first step;
    obtaining a first region segmentation result by performing region segmentation for each of the groups by using the threshold;
    performing filtering processing on the one or more of the R image, the G image, and the B image, for each of the groups specified in the third step;
    obtaining a second region segmentation result by performing threshold processing on values obtained through the filtering processing thus selected; and
    extracting the second object region, by performing a logical OR operation by using the first region segmentation result and the second region segmentation result.

8. The method for region segmentation of urine particle image according to claim 2,
    wherein for a group specified in the third step as being classified into a predetermined group, the region segmentation result obtained in the second step is outputted in the fourth step.

9. An apparatus for region segmentation of a urine particle image, comprising:
    a means for extracting a first object region larger than an object particle included therein, from a urine particle image taken by an image input optical system, by using at least one of a red (R) image of the urine particle image, a green (G) image of the urine particle image, and a blue (B) image of the urine particle image;
    a means for calculating a size of the first object region based on at least one of an area or a perimeter of the first object region and a density distribution of the first object region, in the first object region, of each of the at least one of the R image, the G image, and the B image, and for classifying the first object region into one group of a predetermined number of groups, based on the size of the first object region, and the density distribution of the first object region; and a means for extracting a second object region, representing the object particle, from the first object region, by using group-specific region segmentation, including use of the at least one of the R image, the G image, and the B image.

* * * * *